United States Patent
Kaneda et al.

(10) Patent No.: US 8,418,564 B2
(45) Date of Patent: Apr. 16, 2013

(54) PROPERTY TESTING APPARATUS FOR PHOTOCURABLE RESIN, RETAINER USED IN THE TESTING APPARATUS AND PROPERTY TESTING METHOD

(75) Inventors: Masaki Kaneda, Kyoto (JP); Masaru Nakagawa, Sendai (JP); Akihiro Kohno, Niigata (JP)

(73) Assignees: Shimadzu Corporation, Kyoto-shi, Kyoto (JP); Tohoku Technoarch Co., Ltd., Sendai-shi, Miyagi (JP)

( * ) Notice: Subject to any disclaimer, the term of this patent is extended or adjusted under 35 U.S.C. 154(b) by 302 days.

(21) Appl. No.: 12/870,235

(22) Filed: Aug. 27, 2010

(65) Prior Publication Data

US 2011/0056310 A1    Mar. 10, 2011

(30) Foreign Application Priority Data

Sep. 7, 2009 (JP) ................ 2009-206133

(51) Int. Cl.
     *G01L 1/24*        (2006.01)
(52) U.S. Cl.
     USPC ................................. 73/800; 73/760
(58) Field of Classification Search .......... 73/760, 73/800, 862.624
See application file for complete search history.

(56) References Cited

U.S. PATENT DOCUMENTS

| | | | |
|---|---|---|---|
| 5,359,899 A | 11/1994 | Nishimura et al. | |
| 5,463,212 A * | 10/1995 | Oshima et al. | 235/468 |
| 5,909,266 A * | 6/1999 | Matsuo et al. | 349/187 |
| 6,049,643 A * | 4/2000 | Lee et al. | 385/28 |
| 6,523,397 B1 | 2/2003 | Tosaki | |
| 7,307,118 B2 * | 12/2007 | Xu et al. | 524/463 |
| 2002/0130989 A1 * | 9/2002 | Nakao et al. | 349/86 |
| 2004/0011457 A1 * | 1/2004 | Kobayashi et al. | 156/272.2 |

FOREIGN PATENT DOCUMENTS

| | | |
|---|---|---|
| CN | 1531016 A | 9/2004 |
| CN | 101465292 A | 6/2009 |
| JP | 07-072062 A | 3/1995 |
| JP | 10-291231 A | 11/1998 |
| KR | 0126455 B1 | 12/1993 |

OTHER PUBLICATIONS

Korean Office Action dated Jan. 17, 2012, issued in corresponding Korean Patent Application No. 10-2010-0081419.
Chan, Edwin P. et al. "Quantifying Release in Step-and-flash Imprint Lithography," J. Vac. Sci Technol. B, vol. 24, No. 6, Nov./Dec. 2006, pp. 2716-2722.
Taniguchi, Jun et al. "Measurement of Adhesive Force Between Mold and Photocurable Resin in Imprint Technology," Jpn. J. Appl. Phys. vol. 41 No. 6B, pt. 1, 2002, pp. 4194-4197.
Chinese Office Action dated Aug. 29, 2012, issued in corresponding Chinese Patent Application No. 201010269983.0, with English translation (9 pages).

* cited by examiner

*Primary Examiner* — Max Noori
(74) *Attorney, Agent, or Firm* — Westerman, Hattori, Daniels & Adrian, LLP

(57) ABSTRACT

A retainer for use in measuring a force generated between a photocurable resin and a pressing member by a detector includes: a pressing member that has light transmission characteristics and is pressed to the photocurable resin; and a light irradiation block that is provided between the detector and the pressing member and irradiates light emitted from an external light source onto the pressing member in a state of being not contacting a light source and an optical transmission line including an optical fiber.

11 Claims, 8 Drawing Sheets

PROPERTY TESTING APPARATUS FOR PHOTOCURABLE RESIN, RETAINER USED IN THE TESTING APPARATUS AND PROPERTY TESTING METHOD

INCORPORATION BY REFERENCE

The disclosures of the following priority applications is herein incorporated by references:

Japanese Patent Application No.2009-206133 filed Sep. 7, 2009.

BACKGROUND OF THE INVENTION

1. Field of the Invention

The present invention relates to a testing apparatus for testing a property of photocurable resin, a retainer used in such a testing apparatus, and a method for testing a property of a photocurable resin.

2. Description of Related Art

Heretofore, properties of photocurable resins upon release, represented by peeling force, have been studied. Measurement of properties of photocurable resins disclosed in "Measurement of Adhesive Force Between Mold and Photocurable Resin in Imprint Technology (Jpn. Appl. Phys. Vol. 41 (2002) pp. 4194-4197) (Hereafter, Reference 1) are conducted by the following procedure.

(a) A photocurable resin is dripped on one of rectangular glass substrates (hereafter, "first substrate") by a device that drips the photocurable resin and the other of the rectangular glass substrates (hereafter, "second substrate") is placed on its edge on the first substrate so that the second substrate is adhered perpendicular to the first substrate.

(b) A pair of the glass substrates adhered with the photocurable resin is transported to a testing apparatus and set therein so that the first substrate is held on its both ends.

(c) Ultraviolet light is irradiated to the photocurable resin through the glass substrate to cure the photocurable resin.

(d) Thereafter, a test force is applied on both edges of the second substrate in a direction departing from the first substrate and peeling force of the cured photocurable resin is measured.

The property measuring method disclosed in "Quantifying release in step-and-flash imprint lithography: J. Vac. Sci. Technol. B 24(6), Nov/Dec 2006" (Hereafter, Reference 2) is conducted by using a testing apparatus and a jig described as follows. This testing apparatus includes a table that retains a template on a surface of which a photocurable resin is dripped, an ultraviolet light irradiating device that irradiates ultraviolet light to the photocurable resin through the template from beneath the table, a hemisphere pressing jig (hemispherical superstrate) that contacts the photocurable resin dripped on the surface of the template on the table, and an elevating machine that moves the pressing jig up and down through a load cell.

The procedure of the property measuring method disclosed in Reference 2 is as follows.

(a) On a surface of a template (which is an element corresponding to a stamper) held on a table is dripped a photocurable resin.

(b) The hemisphere pressing jig is moved down by means of the elevating machine to have the hemisphere made of a resin of about 2 mm in diameter contacted the photocurable resin and ultraviolet light is irradiated thereon.

(c) After the photocurable resin is cured, the hemisphere pressing jig is moved up by the elevating machine to take the hemisphere off from the template. On this occasion, the photocurable resin that has been cured between the template and the hemisphere is peeled off from the template and transferred to the hemisphere as the hemisphere is moved.

SUMMARY OF THE INVENTION

The testing apparatus disclosed in Reference 1 is difficult to set a rectangular glass substrate therein without tilting the rectangular glass substrate when it is transported from a place where the photocurable resin is dripped to the testing apparatus. That is, tilting angles of the two rectangular glass substrates and the tilting angle of the load axis of the testing apparatus unavoidably have errors, so that it is difficult to apply a force in a direction perpendicular to the two rectangular glass substrates. Moreover, when a force is applied so that one of the rectangular substrates is separated from the other, the glass substrates undergo deflection. As a result, there arise problems on reproducibility of tests and reliability of the obtained data.

The testing apparatus disclosed in Reference 2 uses a hemisphere made of a resin having a low Young's modulus as a pressing jig. This is not a combination of quartz and resin as in the actual procedure. The up and down of the jig is in reverse to that in the actual process. Therefore, the effect of surface segregation of the releasing agent added to the photocurable resin is not reflected to the measured data. Furthermore, the radius of the hemisphere is 2 mm, which are quite different from the conditions used in the actual process, so that there would be a problem on the accuracy of data.

According to a first aspect of the present invention, a retainer for use in measuring a force generated between a photocurable resin and a pressing member by a detector includes: a pressing member that has light transmission characteristics and is pressed to the photocurable resin; and a light irradiation block that is provided between the detector and the pressing member and irradiates light emitted from an external light source onto the pressing member in a state of being not contacting a light source and an optical transmission line including an optical fiber.

According to a second aspect of the present invention, it is preferred that the light irradiation block in the retainer according to the first aspect preferably includes an attachment unit at which the pressing member is interchangeably attached, the attachment unit being disposed on a lower surface of the light irradiation block.

According to a third aspect of the present invention, the attachment unit in the retainer according to the second aspect may be constructed such that the pressing member is movable within a predetermined gap according to contraction accompanied by curing of the photocurable resin.

According to a fourth aspect of the present invention, the light irradiation block in the retainer according to the second aspect preferably includes a light introduction window through which light emitted from the external light source is introduced; and a reflection mirror that guides light from the external light source introduced through the light introduction window toward the photocurable resin through the pressing member.

According to a fifth aspect of the present invention, it is preferred that the pressing member in the retainer according to the first aspect preferably has a resin contact surface, which is a spherical surface.

According to a sixth aspect of the present invention, a testing apparatus for measuring a force generated between a photocurable resin and a pressing member, includes: a retainer according to the first aspect; a detector that measures the force; a substrate retaining mechanism that retains a substrate on which the photocurable resin is dripped; and a movement mechanism that relatively moves the photocurable resin and the pressing member.

According to a seventh aspect of the present invention, the testing apparatus according to the sixth aspect may be such that when light from the external light source is irradiated through the pressing member to the photocurable resin, the detector measures the force manifesting a contractile force of the photocurable resin, the force being generated between the photocurable resin and the pressing member.

According to an eighth aspect of the present invention, the testing apparatus according to the sixth aspect may be such that after light from the external light source is terminated to irradiate through the pressing member to the photocurable resin, the movement mechanism relatively moves the substrate and the pressing member in a predetermined constant speed, and the detector measures the force manifesting a peeling force of the photocurable resin, the force being generated between the photocurable resin and the pressing member during moving of the substrate and the pressing member in the predetermined constant speed.

According to a ninth aspect of the present invention, the testing apparatus according to the sixth aspect may further include: a gas feeding member that spray an inert gas, wherein a space surrounded by the substrate, the pressing member, and the gas feeding member is substituted by the inert gas.

According to a tenth aspect of the present invention, a method of testing a property of a photocurable resin by measuring a force generated between the photocurable resin and a pressing member, the method comprising: dripping the photocurable resin on a substrate; pressing the dripped photocurable resin with a pressing member that has light transmission characteristics; irradiating light emitted from an external light source onto the pressing member through the pressing member in a state of being not contacting a light source and an light transmission line including an optical fiber; and detecting a force generated between the pressing member and the photocurable resin.

According to an eleventh aspect of the present invention, the property testing method according to the tenth aspect may be such that the generated force is detected with positional relationship between the pressing member and the substrate being fixed.

DESCRIPTION OF PREFERRED EMBODIMENT

Figure 1:
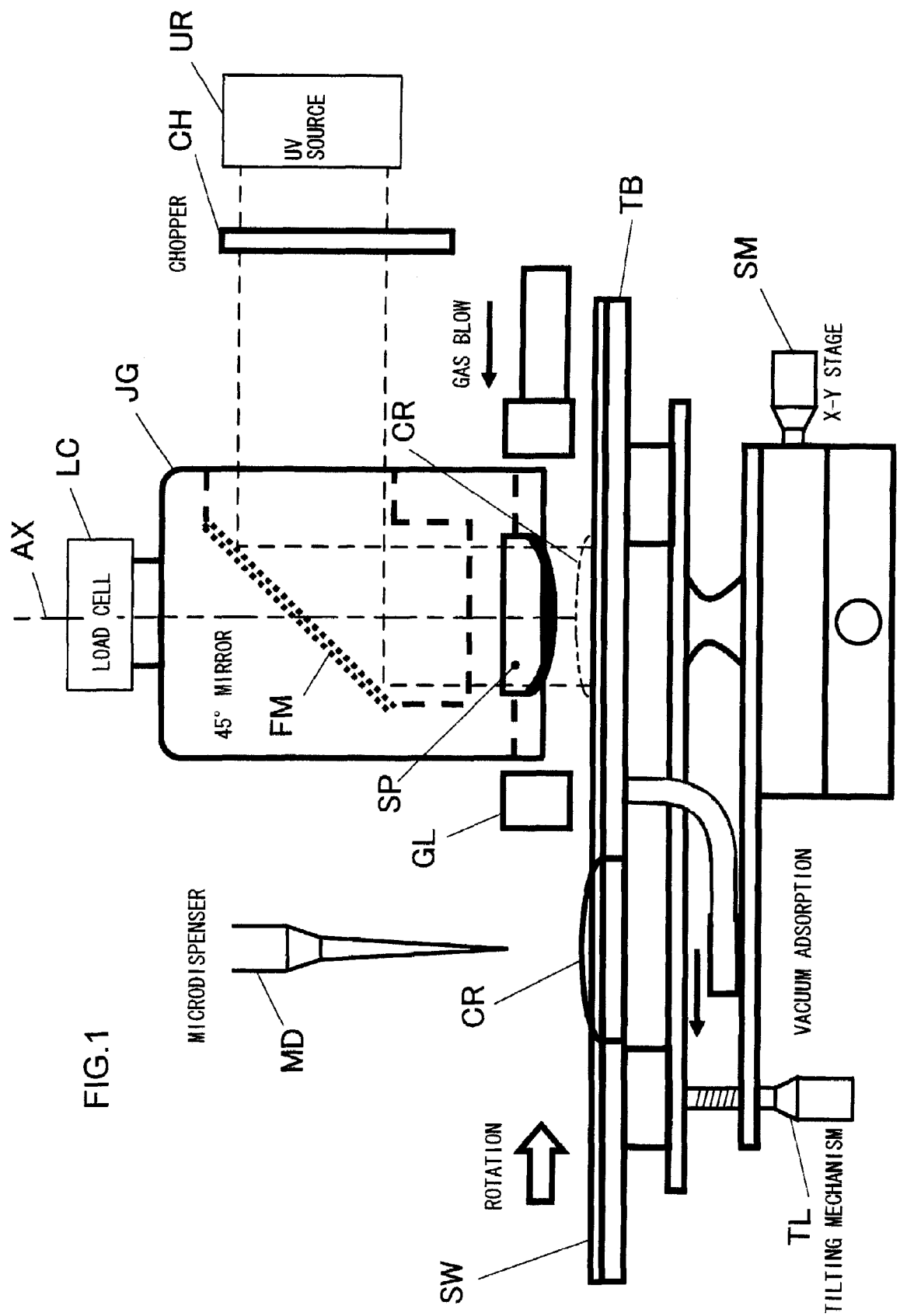
FIG. 1 is a diagram schematically showing a construction of a testing apparatus for evaluating various properties of a photocurable resin.

The property testing apparatus for measuring a property of a photocurable resin according to the present invention is explained with reference to FIG. 1, which shows a schematic construction of the apparatus.

A predetermined amount of photocurable resin CR is dripped from a microdispenser MD onto a silicon wafer SW that is vacuum-sucked on a turntable TB. The turntable TB is rotated so that the dripped photocurable resin CR comes to be in alignment with an axis AX of a retainer JG. A gas feeding ring GL is arranged coaxially with the axis AX. On a lower side of the retainer JG is attached a pressing member SP having a spherical pressing surface that contacts the photocurable resin. The retainer JG is lowered to a predetermined fixed position by an elevating device (not shown) so that a gap between the silicon wafer SW and the pressing member SP is set to a predetermined value, and the pressing member SP is pressed against the photocurable resin CR to contact it. The gap or clearance between the silicon wafer SW and the pressing member SP is fixed.

When an inert gas (for example, nitrogen or helium) is sprayed from the gas feeding ring GL, the space surrounded by the silicon wafer SW, the gas feeding ring GL, and the pressing member SP becomes an inert gas atmosphere. Then, the gas spray is stopped, a chopper CH is opened, and ultraviolet light (or UV light) is introduced from an external ultraviolet light source (or UV source) UR into the retainer JG. The ultraviolet light incident to the retainer JG is reflected downward by a full reflection mirror FM, transmitted through the pressing member SP, and irradiated onto the photocurable resin CR. The photocurable resin CR that has received ultraviolet light starts to cure and contract. As a result, the retainer JG is drawn downward depending on an adhesive force between the pressing member SP and the photocurable resin CR and a contractile force of the photocurable resin CR. Since the retainer JG is attached to a load cell LC, a tensile force can be detected by using the load cell LC.

The retainer JG is provided between the load cell LC and the pressing member SP and serves as a light irradiation block that irradiates ultraviolet light emitted from an external light source UR toward the pressing member SP in a state of not contacting an optical transmission line such as an optical fiber.

The reason why an inert gas atmosphere is used when the photocurable resin is cured is as followed. That is, when a photo-radical-polymerizable resin is used as the photocurable resin, it is preferred that oxygen that inhibits the polymerization is removed. Accordingly, in this embodiment, a quasi-sealed space is formed by surrounding the photocurable resin dripped on the silicon wafer SW by the gas feeding ring GL and the space is substituted by an inert gas before ultraviolet light is irradiated for curing the photocurable resin.

In case a photo-cation-polymerizable resin is used as the photocurable resin, it is preferred that the photocurable resin is irradiated with light in an atmosphere from which moisture has been removed. For this purpose, an inert gas is supplied in order to dry the above-mentioned space.

In FIG. 1, a tilting mechanism TL is provided, which mechanism is designed to adjust the tilt of the silicon wafer SW and make the silicon wafer SW locate perpendicular to the axis AX. X-Y-axis adjusting stage (X-Y stage) SM is a device that adjust the position of the turntable TB in both X-axis and Y-axis direction with respect to the axis AX.

Figure 2:
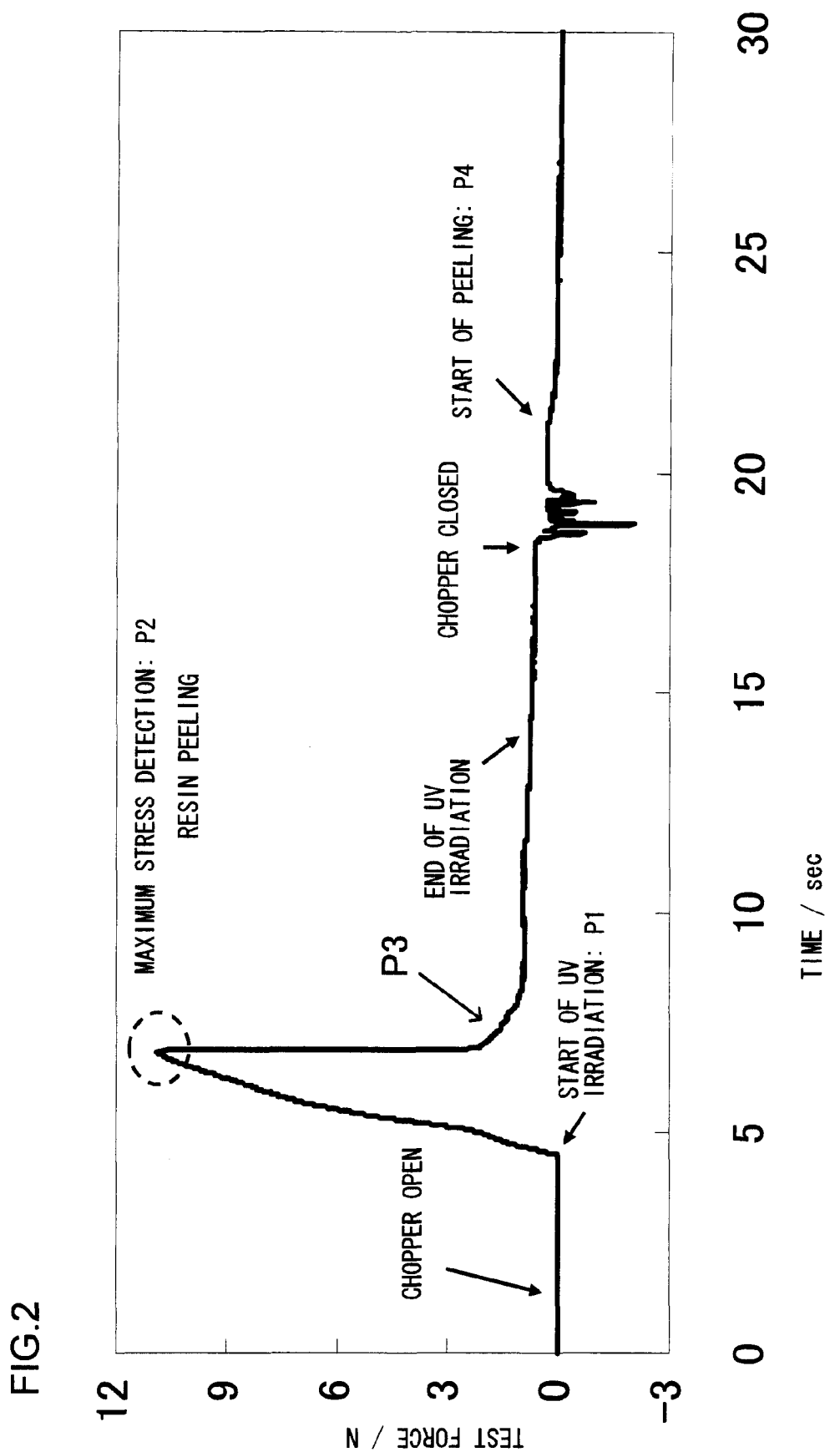
FIG. 2 is a graph showing results of measurement of contraction stress.

FIG. 2 is a graph showing results of measurement of a test force when ultraviolet light is irradiated to the photocurable resin CR without changing the position of the retainer JG in the axial direction. This is intended to measure contractile stress of the photocurable resin CR.

The retainer JG is lowered and the distance between the pressing member SP and the silicon wafer SW is set to a predetermined value. On this occasion, the pressing member SP contacts the photocurable resin CR. About 5 seconds after the start of the test, ultraviolet light irradiation (or UV irradiation) is started (which is referred to as "Event P1"). The test force is increased as from 0 to a maximum value of about 11 N (which is referred to as "Event P2"), and then abruptly decreased to about 1 N (which is referred to as "Event P3"). Thereafter, the ultraviolet light irradiation is terminated. After about 22 seconds, the retainer JG starts to be moved upward at a constant speed. There occurs peeling between the pressing member SP and the photocurable resin and the test force becomes 0 (which is referred to as "Event P4").

Between Event P1 and Event P2, the photocurable resin CR having received irradiation with ultraviolet light is rapidly cured to start contraction. On this occasion, the retainer JG is drawn downward in response to the adhesive force between the pressing member SP and the photocurable resin CR and to the contractile force of the photocurable resin CR. When the contractile force approaches to the adhesive force, the cured photocurable resin CR starts peeling off from the pressing member SP and the test force is decreased to about 1 N. Thereafter, from Event P3 to Event P4, there is no substantial change in the relationship between the contractile force and the adhesive force. At Event P4, the pressing member SP provided with the retainer JG starts to be moved upward at a constant speed, so that the photocurable resin CR that is in contact with the pressing member SP under a force of about 1N is completely peeled off from the pressing member SP.

A result of division of the maximum test force in FIG. 2 by a surface area at which the pressing member SP is in contact with the photocurable resin gives a contractile force per unit area of the photocurable resin.

Figure 3:
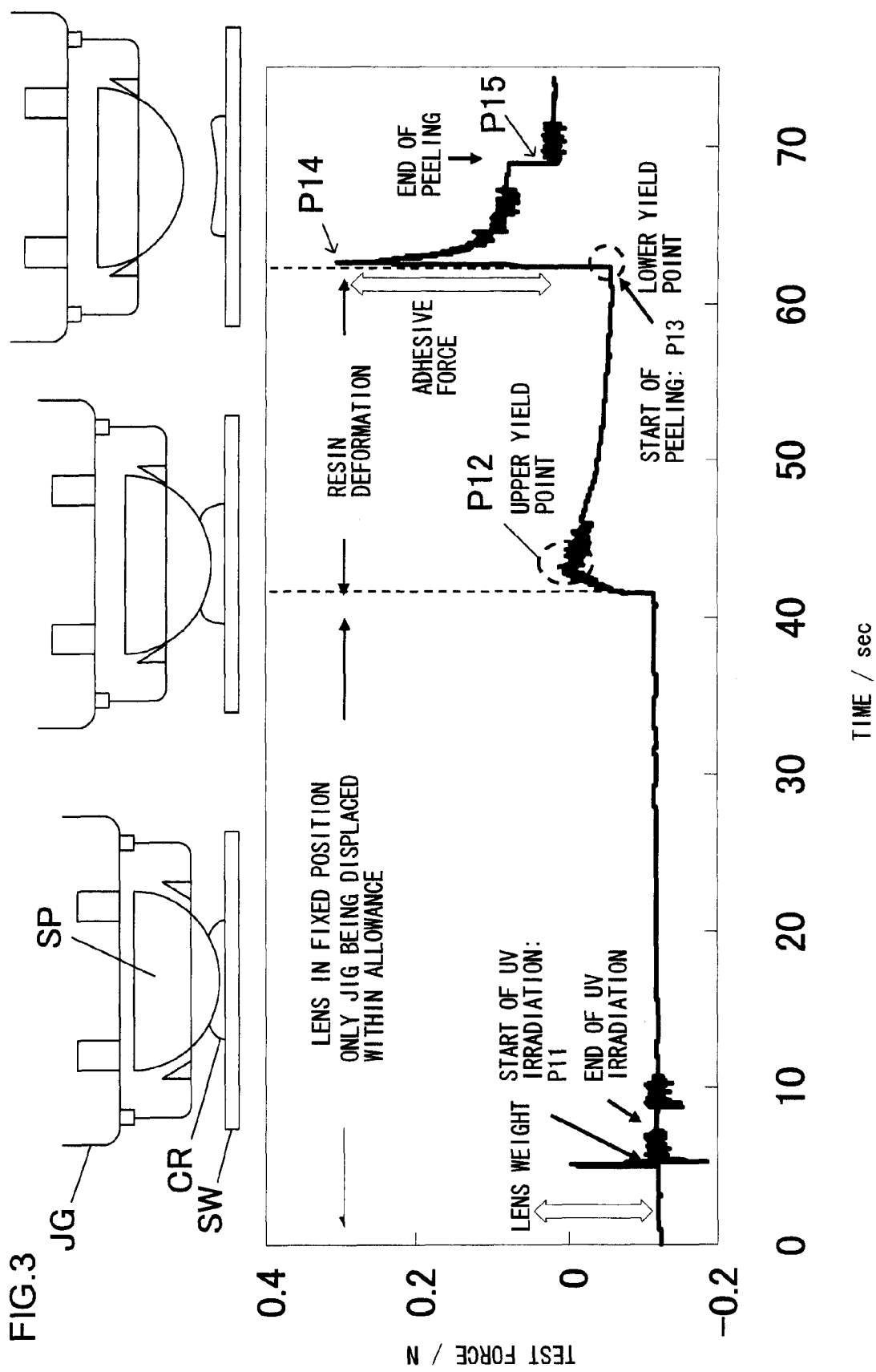
FIG. 3 is a graph showing results of measurement of peeling force.

FIG. 3 presents a graph showing results of measurement of a test force in case the position of attachment of the pressing member SP is set with some allowance in order to cancel the test force to be generated accompanying the contraction of the photocurable resin upon the irradiation of ultraviolet light. This is intended to measure a peeling force of the photocurable resin CR.

The retainer JG is lowered and the distance between the pressing member SP and the silicon wafer SW is set to a predetermined value. On this occasion, the pressing member SP contacts the photocurable resin CR. After the test is started, the test force is about −0.13 N. This value corresponds to the deadweight of the pressing member SP. About 5 seconds after the start of the test, the chopper CH is opened to start irradiation of ultraviolet light (which is referred to as "Event P11"). After about 9 seconds, the irradiation of ultraviolet light is terminated. After the irradiation with light, the retainer JG starts to be moved upward at a constant speed.

Note that curing of the photocurable resin CR starts accompanying the irradiation of ultraviolet light. The pressing member SP that is adhered to the photocurable resin CR is relatively moved with respect to the body of the retainer JG in response to contraction of the photocurable resin CR due to allowance of the attachment mechanism. As shown in an upper part of FIG. 3, the pressing member SP has an allowance with which the pressing member SP is moved in the axial direction AX within the retainer JG.

The reason why a load cell output at the start of the test is −0.13 N as shown in FIG. 3 is explained. That is, zero point adjustment of the output of the load cell is performed by zero-resetting the output value of the load cell when the deadweight of the retainer inclusive of the deadweight of the pressing member SP is applied. Therefore, when the retainer JG is contacted with the photocurable resin, the pressing member SP is relatively moved upward with respect to the body of the retainer JG due to the viscosity of the resin, so that the deadweight of the pressing member SP does not act on the load cell LC. As a result, the load cell LC manifests an output value of −0.13 N.

About 40 seconds after the start of the test, the allowance of the pressing member SP is lost and the test force becomes about 0 N (which is referred to as "Event P12"). This is because the force corresponding to the deadweight of the pressing member SP is applied to the retainer JG accompanying the loss of the allowance of the pressing member SP. Thereafter, too, the retainer JG is moved upward at a constant speed, so that when the pressing member SP that is adhered with the photocurable resin CR is peeled off from the photocurable resin CR (which is referred to as "Event P13"), the test force is abruptly increased to about 0.3 N (which is referred to as "Event P14"). Thereafter, when the photocurable resin CR is peeled off from the pressing member SP, the test force becomes approximately 0 N (which is referred to as "Event P15").

After the test force manifests a maximum value in the Event P14, the test force is not abruptly decreased toward 0 N. This is presumed to be due to the fact that peeling does not occur simultaneously at all contact points between the pressing member SP and the photocurable resin CR but peeling occurs gradually. Note that the test force in Event P14 shown in FIG. 3 may be called a peeling force or an adhesive force.

As mentioned above, the pressing surface of the pressing member SP is formed to be a spherical surface. The reason why is as explained below.

In case a microcircuit of a semiconductor device is fabricated by a nano-imprint lithography method, the microcircuit includes fine structures with line widths of about 20 to 30 nm and a stamper has a repeated structure of unevenness on the order of nano meters. Therefore, when the stamper is pressed against the photocurable resin, the surface of the substrate is deflected by about 1 radian so that no air should be trapped in the space in the uneven structure that could prevent flow-in of the resin. Accordingly, also when tests for evaluation of peeling property and the like of the photocurable resin are performed, it is preferred that some curvature is given to the pressing member.

A testing apparatus that actually measures the above-mentioned properties of a photocurable resin is explained with reference to FIGS. 4 to 8.

Figure 4:
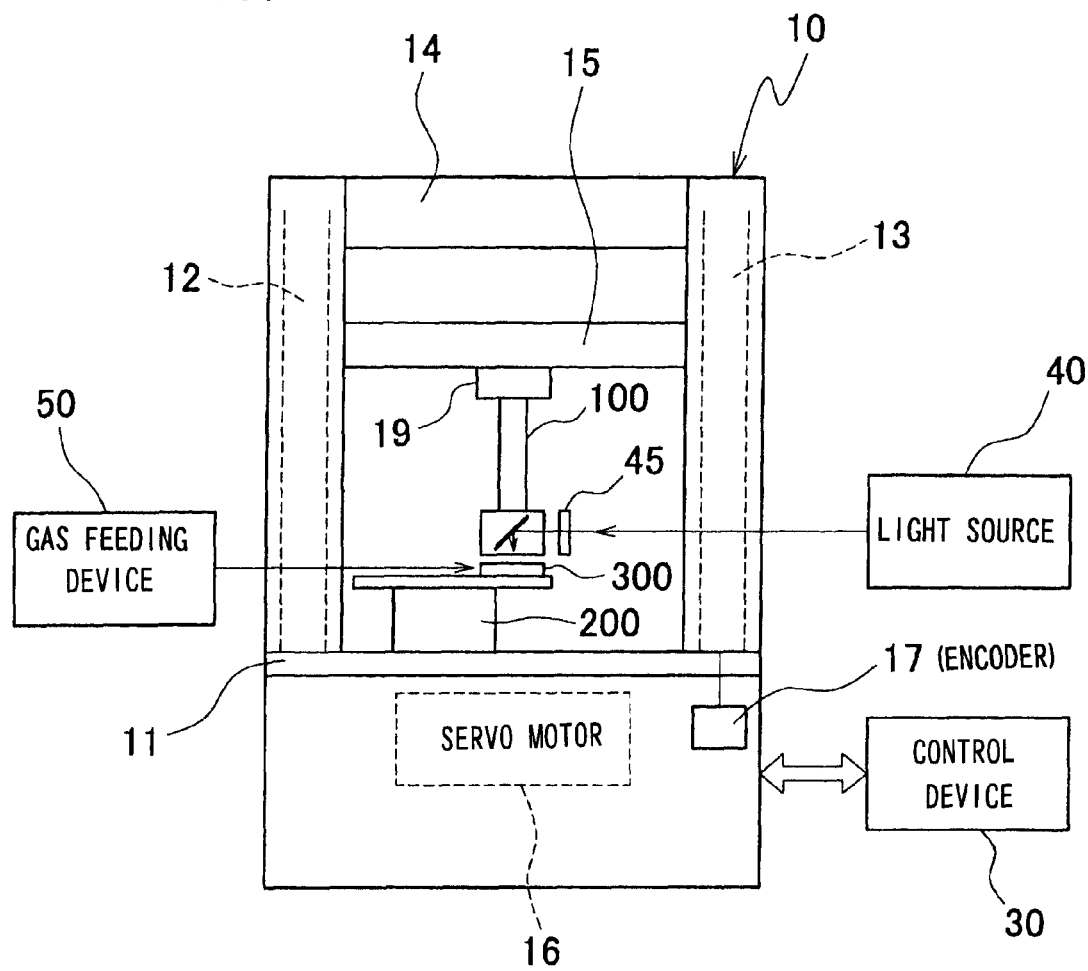
FIG. 4 is a diagram showing a construction of a property testing apparatus according to an embodiment of the present invention.

FIG. 4 shows a property testing apparatus for photocurable resins according to an embodiment of the present invention. The property testing apparatus includes a body 10, a control device 30, a light source 40 that emits ultraviolet light to be irradiated to a photocurable resin, a chopper 45 that guides the ultraviolet light UV emitted from the light source 40 to the photocurable resin CR at arbitrary timing, and a gas feeding device 50 that supplies an inert gas.

The body 10 of the testing apparatus is constructed as follows.

A pair of horizontal screw bars 12 and 13 is provided upright on a fixed table 11. A yoke 14 bridges the screw bars 12 and 13 on their upper ends. A pair of nuts (not shown) is provided on both sides of a crosshead 15 and is screwed together with the screw bars 12 and 13. This allows the crosshead 15 to be supported moveably up and down. The screw bars 12 and 13 are driven by a servo motor 16 arranged at the fixed table 11. The respective members that constitute these have a function to relatively move the pressing member 104 and the substrate SW with respect to each other. The rotation of the screw bar 12 is detected by an encoder 17 and the result is input into a control device 30. The position of the crosshead 15 can be calculated from the output value from the encoder 17.

On the lower side of the crosshead 15 is attached an upper jig 100 via the load cell 19 and a lower jig 200 is attached on the lower side of the fixed table 11 so that the upper jig 100 and the lower jig 200 are opposite to each other, between which the property of the photocurable resin CR is measured. In FIG. 4, a gas feeding ring 300 is used to have the photocurable resin exposed to an inert gas atmosphere when the photocurable resin is irradiated with light.

Figure 5:
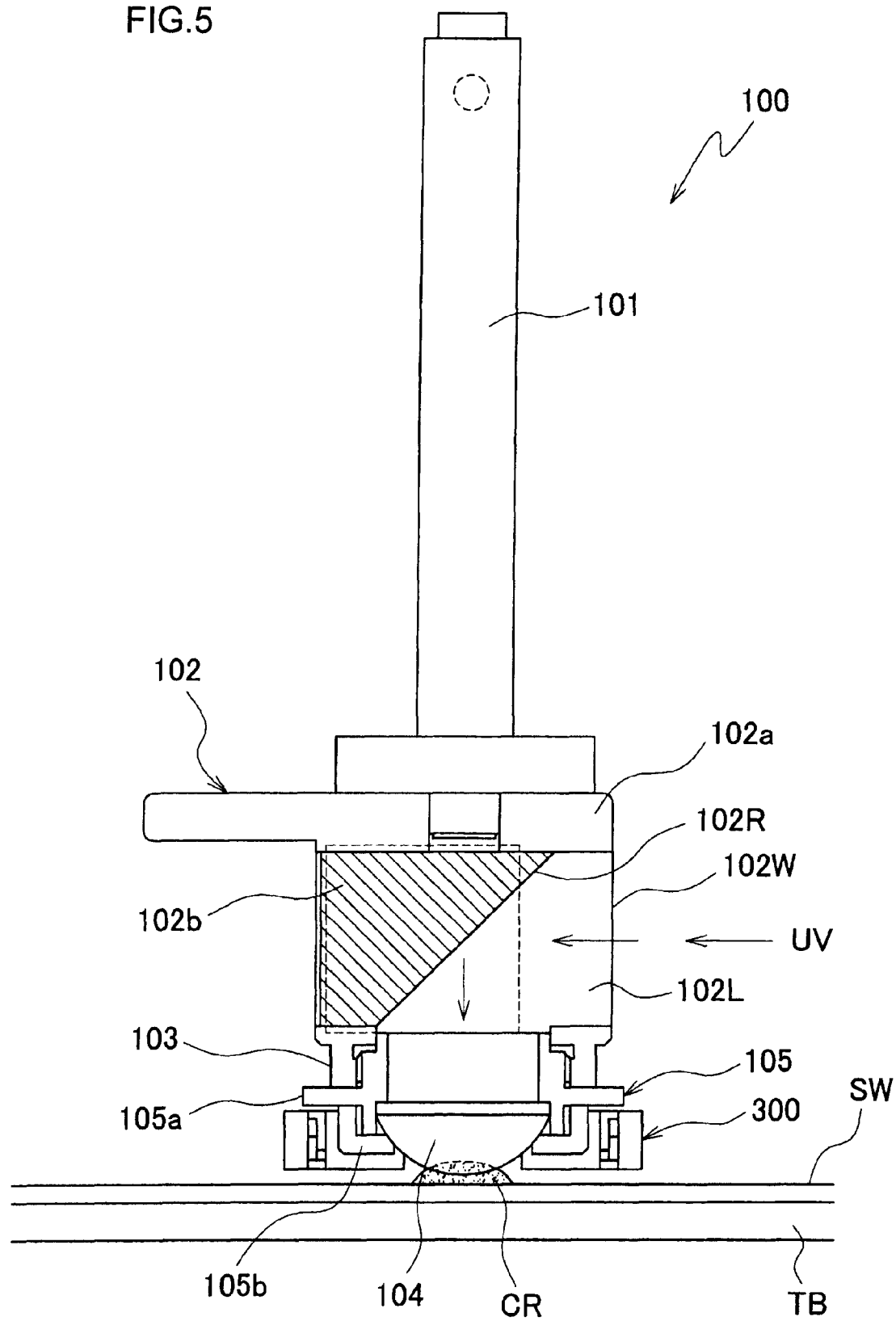
FIG. 5 is a diagram showing details of an upper jig.

As shown in FIG. 5, the upper jig 100 includes a shaft 101 to be attached to the load cell 19, a mirror block 102 provided on the lower end of the shaft 101, an attachment ring 103 provided at the lower end of the mirror block 102 to which a pressing member 104 can be removeably attached, and a pressing sphere holding frame 105 for attaching the pressing member 104 to the attachment ring 103.

The pressing member 104 is a member that has a light transmission characteristics and that is made of quartz glass in the form of a sphere having a contact surface with the photocurable resin of about 16 SR (sphere radius). That is, the pressing member 104 is formed so as to have a shape of a lens.

The mirror block 102 includes a block body 102a formed of an introduction window 102W for ultraviolet light and of a light path 102L, and a cylindrical glass 102b mounted on the block body 102a having a 45°-cut surface on which a reflection film is deposited by vapor deposition to form a reflecting surface 102R. Ultraviolet light UV that has been incident through the introduction window 102W from the right side of the mirror block 102 is reflected downward on the reflecting surface 102R of the cylindrical glass 102b to enter the pressing member 104.

The pressing sphere holding frame 105 includes a pressing sphere holder 105a having a male screw that is threadly mounted on the attachment ring 103 and a retainer ring 105b having a female screw that is threadly mounted on the pressing sphere holder 105a and interchangeably holds the pressing member 104. The retainer ring 105b is threadly mounted on the pressing sphere holder 105a to allow the pressing member 104 to be attached to the pressing sphere holder 105a.

In FIG. 5, the gas feeding ring 300 surrounds the outer periphery of the retainer ring 105b and a flange of the pressing sphere holder 105a is arranged in contact with an upper surface of the gas feeding ring 300. On an inner peripheral surface of the gas feeding ring 300 are provided six gas spray nozzles though which an inert gas, for example, nitrogen or helium is sprayed. As a result, the environment around the photocurable resin CR is substituted by the inert gas, in which environment ultraviolet light is irradiated.

When the inert gas is sprayed from the gas feeding ring 300, the space surrounded by the silicon wafer SW, the gas feeding ring 300, and the pressing member 104 is converted into an inert gas atmosphere. Then, the gas spray is stopped, the chopper 45 is opened, and the ultraviolet light emitted from the external ultraviolet light source UR is introduced to the upper jig 100. The ultraviolet light incident to the upper jig 100 is reflected downward on the reflecting surface 102R and transmitted through the pressing member 104 to irradiate the photocurable resin CR. The photocurable resin CR that has received the ultraviolet light starts to cure and contract. As a result, the upper jig 100 is drawn downward to some extent depending on the adhesive force between the pressing member 104 and the photocurable resin CR and on the contractile force of the photocurable resin CR. The load cell 19 to which the upper jig 100 is attached detects the tensile force that draws the upper jig 100 downward.

The gas feeding ring 300 is provided on a platform (not shown) mounted on the table 11 such that it can swing horizontally. That is, the gas feeding ring 300 is provided on an end of an arm that is rotatably attached to the platform. The position at which the arm is attached to the platform is set in advance such that the gas feeding ring 300 can be held at a predetermined height above the turntable TB. Moreover, the arm is constructed such that it is tilted by about 1° to 2° with respect to a horizontal plane.

Figure 6:
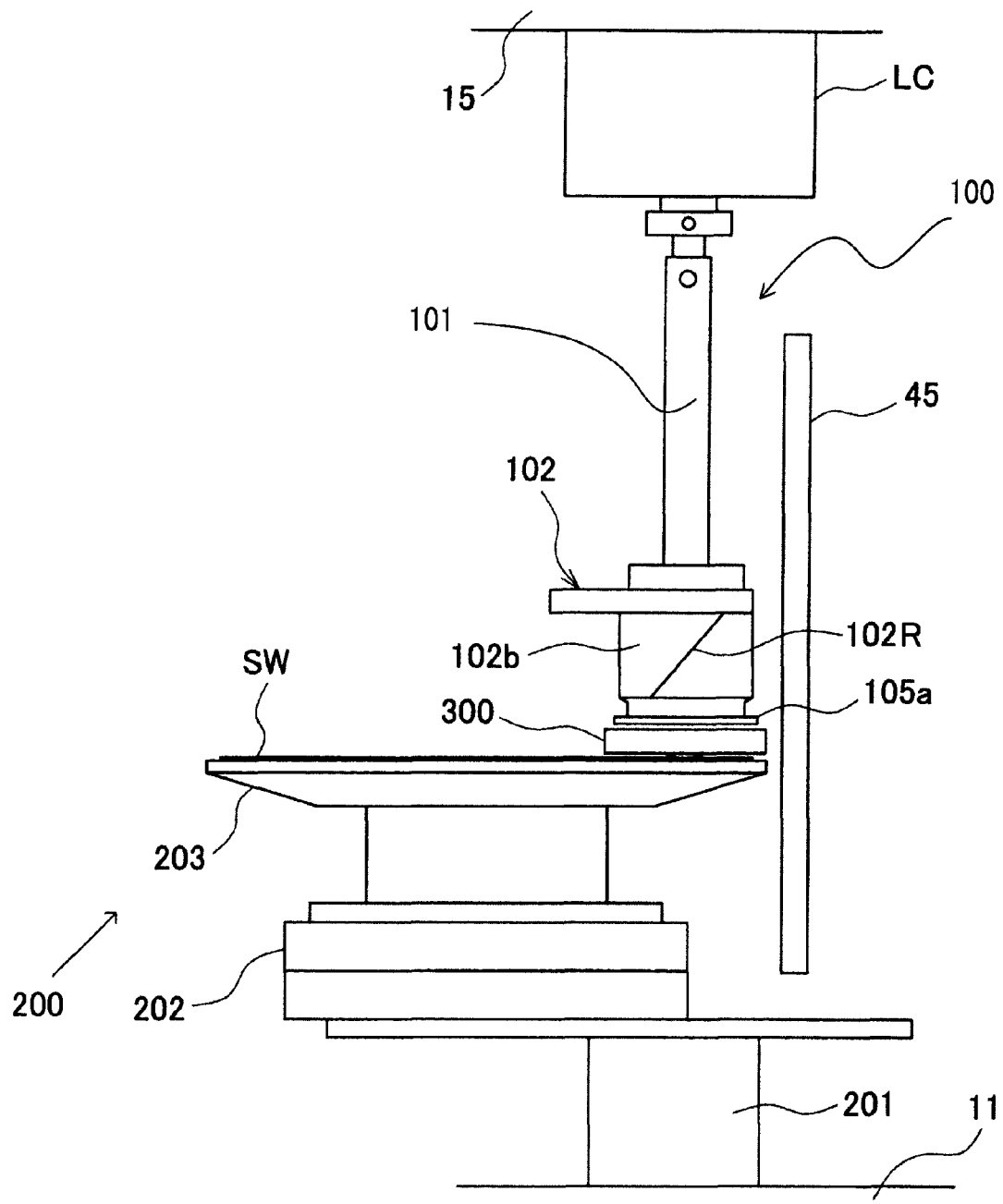
FIG. 6 is a front view showing details of a lower jig.
Figure 7:
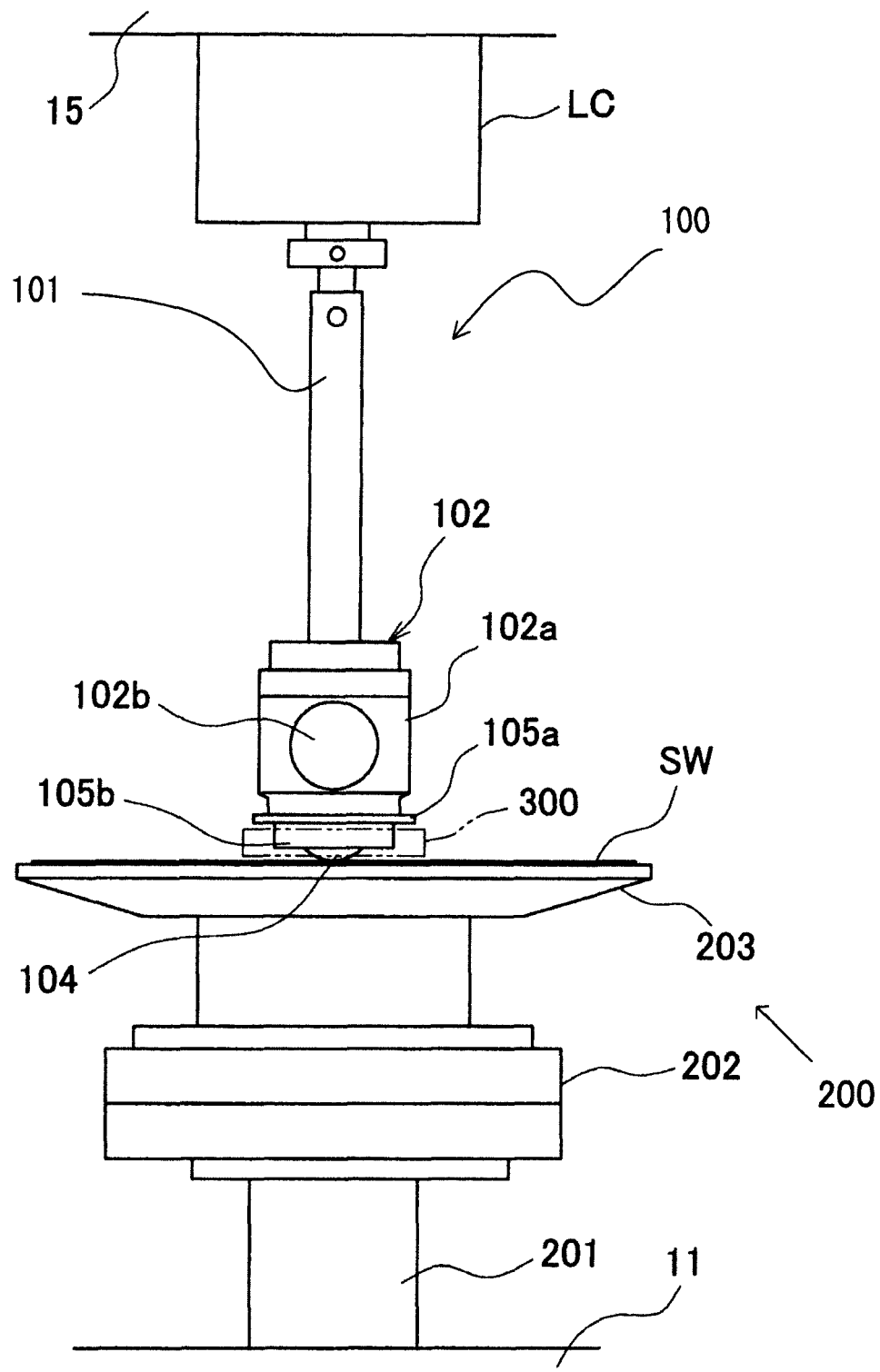
FIG. 7 is a side view showing details of the lower jig.

FIG. 6 presents a front view showing the property testing apparatus and FIG. 7 presents a side view of it, illustrating the lower jig 200.

The lower jig 200 includes a base 201 to be attached to the fixed table 11, an XY stage 202 provided on the base 201 and a circular turntable 203 placed on the XY stage 202. The turntable 203 is provided with a vacuum suction device, with which the silicon wafer SW is sucked and fixed onto the upper surface of the turntable 203. The turntable 203 is provided with an indexing mechanism and when the turntable 203 is manually rotated, a rotation position is defined for every predetermined angle. The rotation operation of the turntable 203 may be linked with the testing apparatus for automation.

The procedure for measuring contraction stress and peeling force of a photocurable resin is explained by using the property testing apparatus as shown in FIG. 4.

-Measurement of Contraction Stress-

To the silicon wafer SW vacuum sucked on the turntable 203 is dripped a predetermined amount of the photocurable resin CR from a microdispenser (not shown). The turntable 203 is rotated manually so that the dripped photocurable resin CR is aligned to the axis (load axis) AX of the upper jig 100. The gas feeding ring 300 is also arranged so that it is coaxial with the axis AX. The upper jig 100 is lowered to a predetermined position so that the distance between the silicon wafer SW and the pressing member 104 can be set to a predetermined value. On this occasion, the pressing member 104 at the end of the jig contacts the photocurable resin CR. The distance between the silicon wafer SW and the pressing member 104 is maintained to be the predetermined value set in advance. Neither the position control nor test force control of the testing apparatus itself is adjusted under the above condition.

When the chopper 45 is opened and the ultraviolet light is introduced into the mirror box 102, the introduced ultraviolet light is reflected downward on the reflecting surface 102R and is irradiated to the photocurable resin CR through the pressing member 104. This causes the photocurable resin CR to start curing. Since the position of the pressing member 104 with respect to the silicon wafer SW is not changed, a test force in the tensile direction is acted onto the upper jig 100 due to the contractile force of the photocurable resin. The tensile test force is detected by the load cell 19. The test force becomes 0 when the photocurable resin CR is peeled off from the pressing member 104.

On this occasion, press indentation of the pressing member 104 is formed on the surface of the photocurable resin. The press indentation is substantially circular in shape and a maximum diameter of the circle is measured, from which a surface area of the press indentation is calculated. A value obtained by dividing the maximum value of the test force measured by the load cell 19 by the surface area of the press indentation is defined to be a contractile force per unit surface area of the photocurable resin.

-Measurement of Peeling Force-

Figure 8:
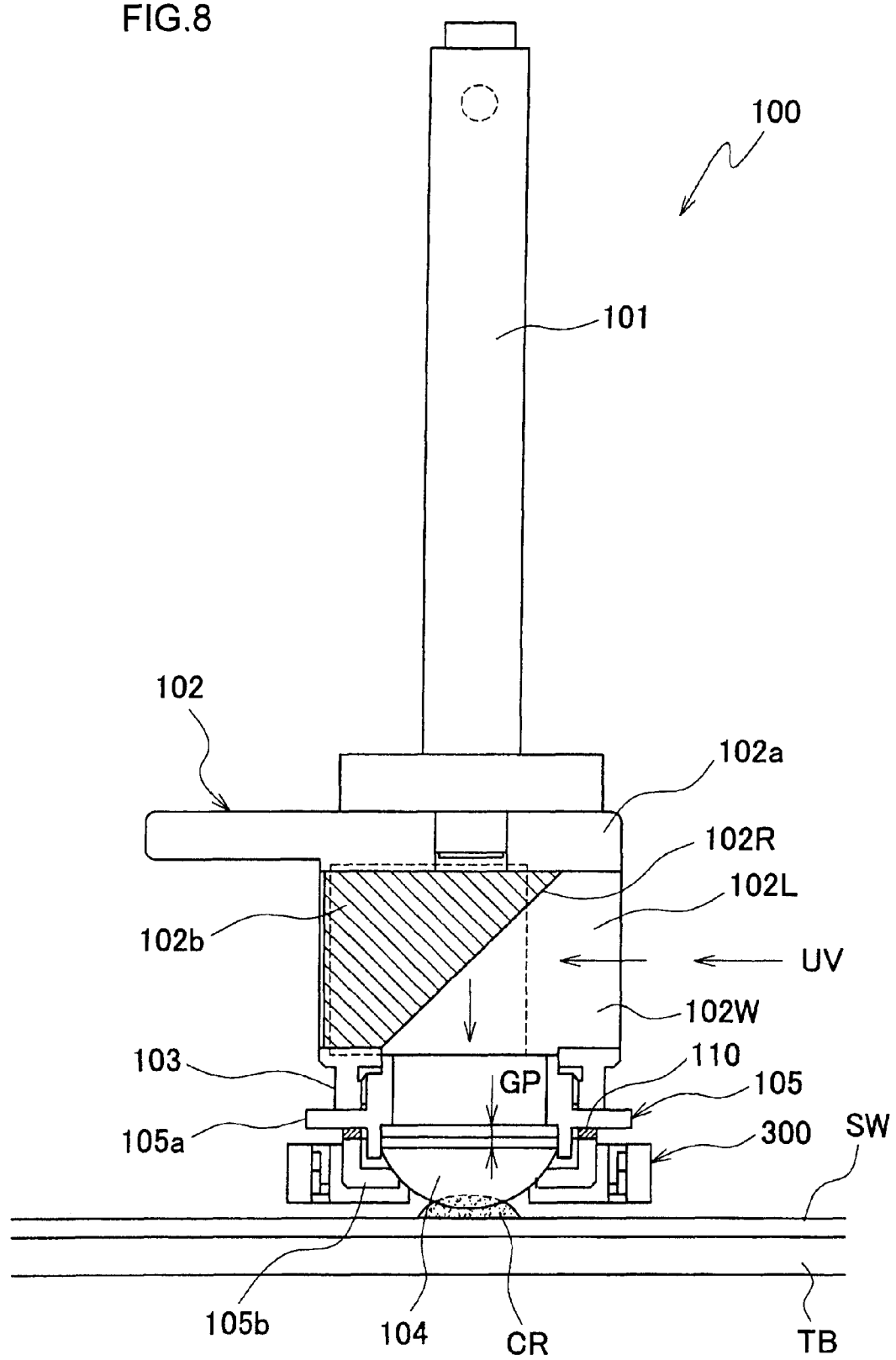
FIG. 8 is a diagram showing details of the upper jig with a pressing hemisphere being moveable with an allowance.

FIG. 8 shows a diagram illustrating a state in which the pressing sphere holder is set such that movement of the pressing member 104 in the direction of axis AX is given an allowance. This is used when measurement shown in FIG. 3 intended to measure a peeling force precisely is performed.

As shown in FIG. 8, the pressing sphere holding frame 105 is constructed such that a spacer 110 is intervened between the retainer ring 105b and the flange of the pressing sphere holder 105a. That is, when the pressing member 104 is attached to the pressing sphere holder 105a with the retainer ring 105b, a ring-shaped spacer 110 is inserted. This allows the pressing member 104 to move up and down by a gap GP.

In the upper jig 100 as shown in FIG. 8, when the crosshead 15 is lowered to cause the pressing member 104 to contact the photocurable resin CR, the pressing member 104 can be moved upward by the repulsion force of the photocurable resin CR. In that condition, when the photocurable resin CR is irradiated with ultraviolet light to cure and contract, the pressing member 104 that has been moved upward is downward moved by an amount of contraction of the photocurable resin CR. On this occasion, the output of the load cell 19 manifests a negative value that correspond to the deadweight of the pressing member 103 as already explained with reference to FIG. 3. At a point in time after several tens of seconds has passed from the irradiation of ultraviolet light that has been performed for a predetermined time, the pressing member 104 is moved upward at a constant speed. As a result, the test force output from the load cell 19 manifests 0 in the same manner as Event P12 described referring to FIG. 3.

Thereafter, the pressing member 104 tends to go away from the photocurable resin CR at a constant speed. However, until a predetermined time passes, the pressing member 104 will not peel off from the photocurable resin and the test force is decreased so as to remove the deflection of the photocurable resin (Events P12 to P13 in FIG. 3). When the pressing means 104 is further moved upward, the photocurable resin CR starts to be peeled off from the surface of the pressing member 104 at a certain point in time (Event P13). Then, at a point in time 10 seconds after it manifests a maximum test force in the event P14, the test force changes and peeling is completed (Event P15).

The property testing apparatus for a photocurable resin having the above-mentioned construction can exhibit the following advantageous effects.

(1) In case ultraviolet light is introduced through an optical fiber cable, the deadweight of the cable affects the results of measurement. In the present embodiment, ultraviolet light emitted from the light source 40 provided as separated from the body 10 of the testing apparatus is introduced into the mirror box 102 in a non-contact state and reflected downward on the reflecting surface 102R in order to be irradiated onto the photocurable resin CR. Therefore, no optical fiber for introducing ultraviolet light is necessary, so that no influence is given to the results of measurement. That is, since the ultraviolet light to be irradiated onto the photocurable resin can be introduced in a state in which it does not contact the pressing member 104, reliability of the measured data is increased.

(2) Quartz glass whose contact surface is of a spherical shape of about 16 SR in radius is selected as the member that contacts the photocurable resin. Therefore, even when the angle between the axis of the upper jig 100 and the silicon wafer SW is deviated from 90°, that is, when an oblique test force is received, no influence is given on the results of measurement. In addition, since the contour of press indentation is a circle, so that the surface area of the press indentation can be calculated without difficulty.

(3) An additive such as a surfactant is added to the photocurable resin in order to improve its releasability. When the additive is segregated on the surface of the photocurable resin, the adhesive force between the pressing member and the resin is a smaller value. On the other hand, when no additive is segregated on the surface of the photocurable resin, the adhesive force between the pressing member and the resin is a larger value. In the property testing apparatus according to the present embodiment, unlike the technology in Reference 2, a test force accompanying peeling between the resin surface on which the additive is segregated and the pressing member is measured as mentioned above, so that the influence of segregation on the surface of the resin can also be evaluated.

The above-mentioned property testing apparatus can be modified as follows.

(1) The mirror box 102 in the upper jig 100 may be changed to have the following construction. That is, an optical fiber introduction space is provided between the load cell and the pressing sphere, and the space is arranged in a direction perpendicular to the axis AX. A light emitting end of the fiber is set in a direction perpendicular to the silicon wafer SW, and the fiber cable is inserted in the jig in a non-contact state.

(2) The construction in which the sphere SP and the pressing member 10 are given allowances may be changed to have the following construction. That is, the position of the jig is controlled such that the test force generated when the photocurable resin CR contracts upon irradiation of ultraviolet light is cancelled and the jig 100 is controlled so as to go away from the photocurable resin CR at a constant speed since a point in time when the contraction is almost completed. With this modified construction, the test force when the photocurable resin CR is peeled off from the pressing member SP can be measured similarly to the case shown in FIG. 3.

(3) In the above-mentioned embodiment, the photocurable resin is dripped on the silicon wafer. However, a glass plate, a quartz plate, a polymer film, a ceramic plate or the like may be used instead of the silicon wafer.

(4) In the above-mentioned embodiment, the resin contact surface of the pressing member is spherical. However, the curvature of the contact surface of the pressing member is not limited to the one used in the embodiment. The resin contact surface of the pressing member may be, for example, planar or a hollow surface.

(5) In the above-mentioned embodiment, the pressing member is made of quartz glass. However, it may be made of a fluorine-contained transparent resin or a cyclic olefin-based polymer.

(6) In the above-mentioned embodiment, the silicon wafer SW is vacuum sucked onto the turntable 203 to hold and fix it. However, various other methods may be used for holding and fixing the silicon wafer.

(7) Although use of the photocurable resin that cures with ultraviolet light is explained above, the present invention is not limited to the property testing apparatus for measuring properties of such a type of resin.

Furthermore, the present invention is not limited to the above-mentioned embodiment unless the features of the present invention are not damaged. Therefore, the jig for measuring a force may be embodied in various forms so far as it relates to a jig for measuring a force used for a property testing apparatus that measures a force generated between a dripped photocurable resin and a pressing member by a detector and tests a property of the photocurable resin, the jig including a pressing member with a light transmission characteristics to be pressed against a photocurable resin dripped on a substrate, and a light irradiation block that is provided between the detector and the pressing member and irradiates light emitted from an external light source toward the pressing member in a state of being not contacting a light source and an optical transmission line such as an optical fiber.

The above described embodiments are examples and various modifications can be made without departing from the scope of the invention.

What is claimed is:

1. A retainer for use in measuring a force generated between a photocurable resin and a pressing member by a detector, comprising:
    a pressing member that has light transmission characteristics and is pressed to the photocurable resin; and
    a light irradiation block that is provided between the detector and the pressing member and irradiates light emitted from an external light source onto the pressing member in a state of being not contacting a light source and an optical transmission line including an optical fiber, wherein
    the light irradiation block includes a light introduction window through which light emitted from the external light source is introduced; and
    a reflection mirror that guides light from the external light source introduced through the light introduction window toward the photocurable resin through the pressing member.

2. A retainer according to claim 1, wherein
    the light irradiation block includes an attachment unit at which the pressing member is interchangeably attached, the attachment unit being disposed on a lower surface of the light irradiation block.

3. A retainer according to claim 2, wherein
    the attachment unit is constructed such that the pressing member is movable within a predetermined gap according to contraction accompanied by curing of the photocurable resin.

4. A retainer according to claim 1, wherein
    the pressing member has a resin contact surface, which is a spherical surface.

5. A testing apparatus that measures a force generated between a photocurable resin and a pressing member, comprising:
    a retainer according to claim 1;
    a detector that measures the force;
    a substrate retaining mechanism that retains a substrate on which the photocurable resin is dripped; and
    a movement mechanism that relatively moves the photocurable resin and the pressing member.

6. A testing apparatus according to claim 5, wherein
    when light from the external light source is irradiated through the pressing member to the photocurable resin, the detector measures the force manifesting a contractile force of the photocurable resin, the force being generated between the photocurable resin and the pressing member.

7. A testing apparatus according to claim 5, wherein
    after light from the external light source is terminated to irradiate through the pressing member to the photocurable resin, the movement mechanism relatively moves the substrate and the pressing member in a predetermined constant speed, and
    the detector measures the force manifesting a peeling force of the photocurable resin, the force being generated between the photocurable resin and the pressing member during moving of the substrate and the pressing member in the predetermined constant speed.

8. A testing apparatus according to claim 5, further comprising:
    a gas feeding member that spray an inert gas, wherein
    a space surrounded by the substrate, the pressing member, and the gas feeding member is substituted by the inert gas.

9. A method of testing a property of a photocurable resin by measuring a force generated between the photocurable resin and a pressing member, the method comprising:
    dripping the photocurable resin on a substrate;
    pressing the dripped photocurable resin with a pressing member that has light transmission characteristics;
    irradiating light emitted from an external light source onto the photocurable resin through the pressing member in a state of being not contacting a light source and an light transmission line including an optical fiber, the light emitted from the external light source being introduced through a light introduction window and being guided by a reflection mirror towards the photocurable resin through the pressing member; and
    detecting a force generated between the pressing member and the photocurable resin.

10. A property testing method according to claim 9, wherein
    the generated force that changes as the photocurable resin cures is detected in a state of positional relationship between the pressing member and the substrate being fixed.

11. A retainer for use in measuring a force generated between a photocurable resin and a pressing member by a detector, comprising:
    a pressing member that has light transmission characteristics and is pressed to the photocurable resin; and
    a light irradiation block that is provided between the detector and the pressing member and irradiates light emitted from an optical fiber onto the pressing member;
    wherein
    the light irradiation block includes an introduction space into which the optical fiber is inserted from a direction perpendicular to an axis of the retainer in a non-contact state, the optical fiber being set so that a light emitting end of the optical fiber is set in a direction perpendicular to the photocurable resin.

* * * * *